United States Patent [19]

Peters et al.

[11] Patent Number: 5,163,598

[45] Date of Patent: Nov. 17, 1992

[54] STERNUM STAPLING APPARATUS

[76] Inventors: Rudolph Peters, 5786 Balmoral Dr., Oakland, Calif. 94619; William Taylor, 8451 San Leandro St., Oakland, Calif. 94621

[21] Appl. No.: 556,276

[22] Filed: Jul. 23, 1990

[51] Int. Cl.⁵ ........................................... A61B 17/064
[52] U.S. Cl. .................... 227/176; 227/19; 227/124; 227/130
[58] Field of Search ............... 227/175, 176, 177, 178, 227/179, 180, 181, 182, 19, 124, 130, 153; 606/75

[56] References Cited

U.S. PATENT DOCUMENTS

| | | | |
|---|---|---|---|
| 3,822,818 | 7/1974 | Strekopytov et al. | 227/19 X |
| 3,960,147 | 6/1976 | Murray | 606/75 |
| 4,444,181 | 4/1984 | Wevers et al. | 606/75 |
| 4,569,469 | 2/1986 | Mongeon et al. | 227/19 |
| 4,617,928 | 10/1986 | Alfranca | 227/180 |
| 4,776,506 | 10/1988 | Green | 227/19 |
| 4,841,960 | 6/1989 | Garner | 606/75 |
| 4,979,954 | 12/1990 | Gwathmey et al. | 227/19 X |

FOREIGN PATENT DOCUMENTS 633522  11/1978  U.S.S.R. ................ 606/75

*Primary Examiner*—Frank T. Yost
*Assistant Examiner*—Rinaldi Rada
*Attorney, Agent, or Firm*—Harris Zimmerman

[57] ABSTRACT

A method and apparatus for stapling together adjacent bone tissue, such as a severed sternum, includes a staple applying tool adapted to drive each leg of a two-legged staple through a respective portion of the bone tissue. The tool includes a distal shoe having a staple forming anvil, the shoe being supported on a thin metal web extending from the tool between the bone tissue portions, so that the tool may be disposed at the outer surface of the bone and the anvil may be supported adjacent to the inner surface of the anvil. The tool includes a piston within caliper assembly, the caliper moving to contact the surface of the sternum and lock in place before the staple is advanced by the piston into the sternum. A staple cartridge is removable from the tool, the cartridge including a latch mechanism that prevents discharge of staples therefrom when the cartridge is removed from the tool. The latch mechanism, which is actuated by insertion into the tool, also acts to retain the cartridge in the tool. The invention also includes an adjusting tool which is provided to increase the impingement of the confronting portions of bone tissue. The adjusting tool includes a pair of jaws, one having a fulcrum lug and the other having two spaced lugs, whereby the staple web may be bent by closure of the lugs together to decrease the linear spacing of the staple legs and increase the abutting force of the bone tissue portions.

33 Claims, 13 Drawing Sheets

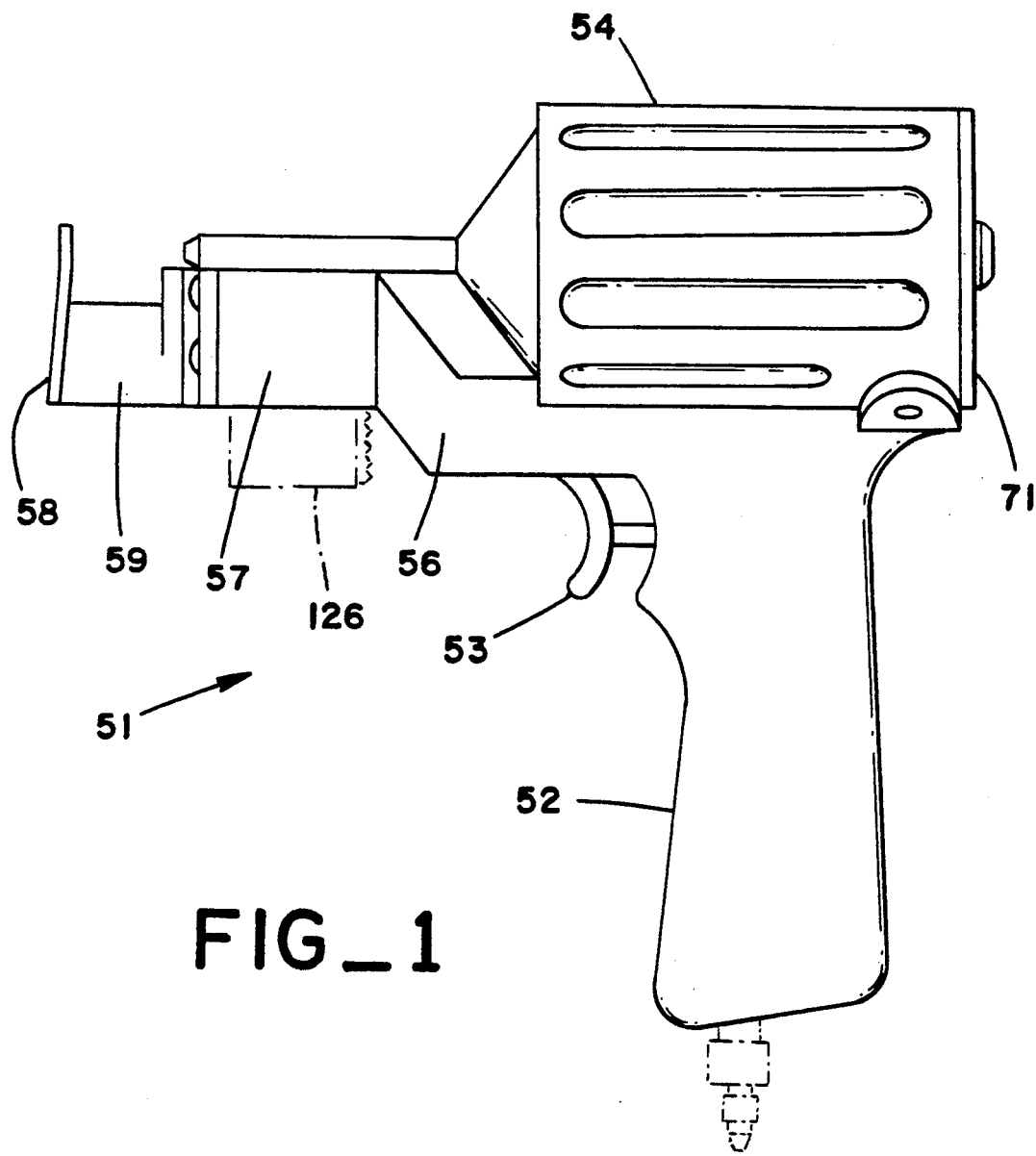
FIG_1
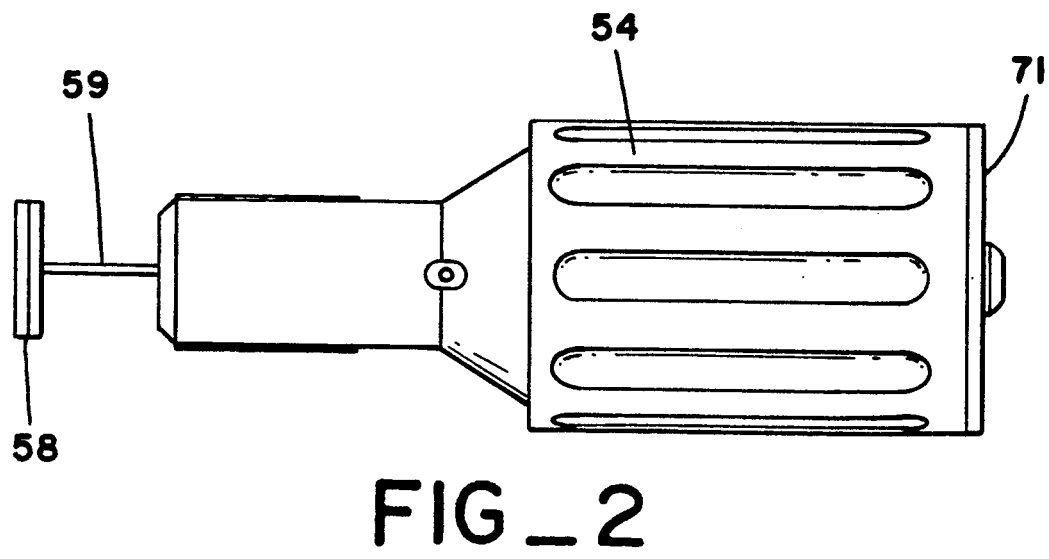
FIG_2

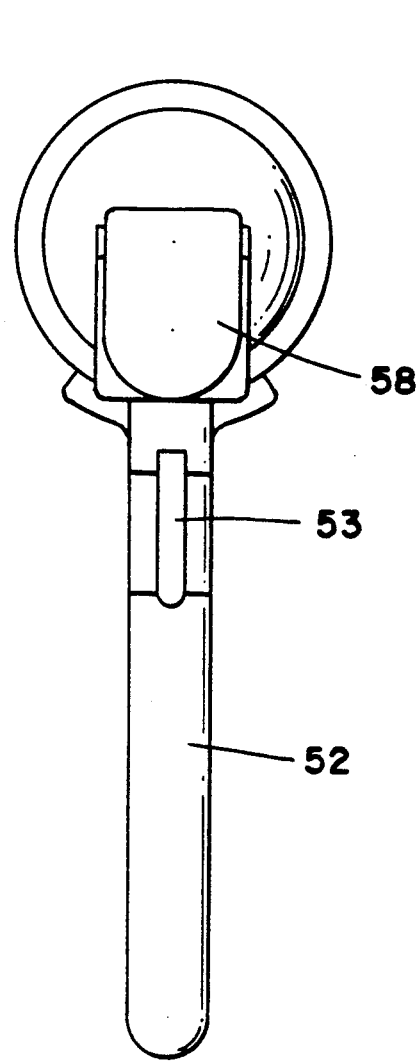
FIG_3
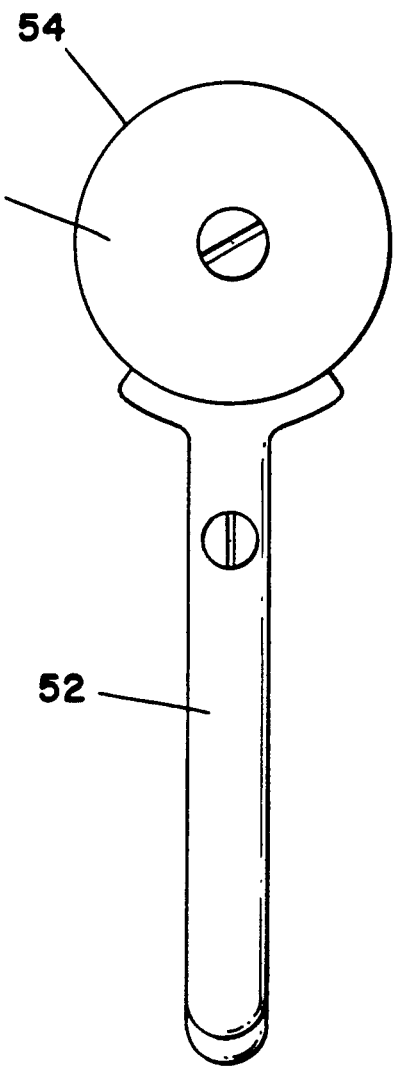
FIG_4
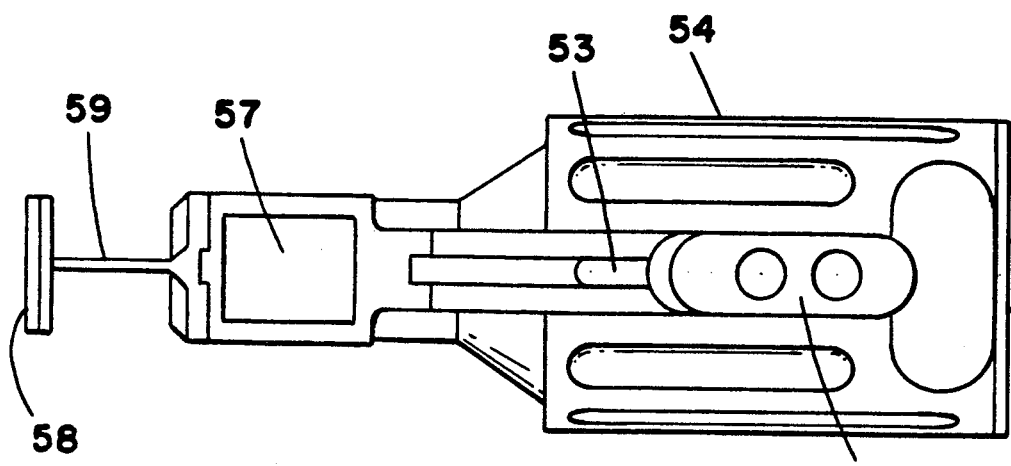
FIG_5

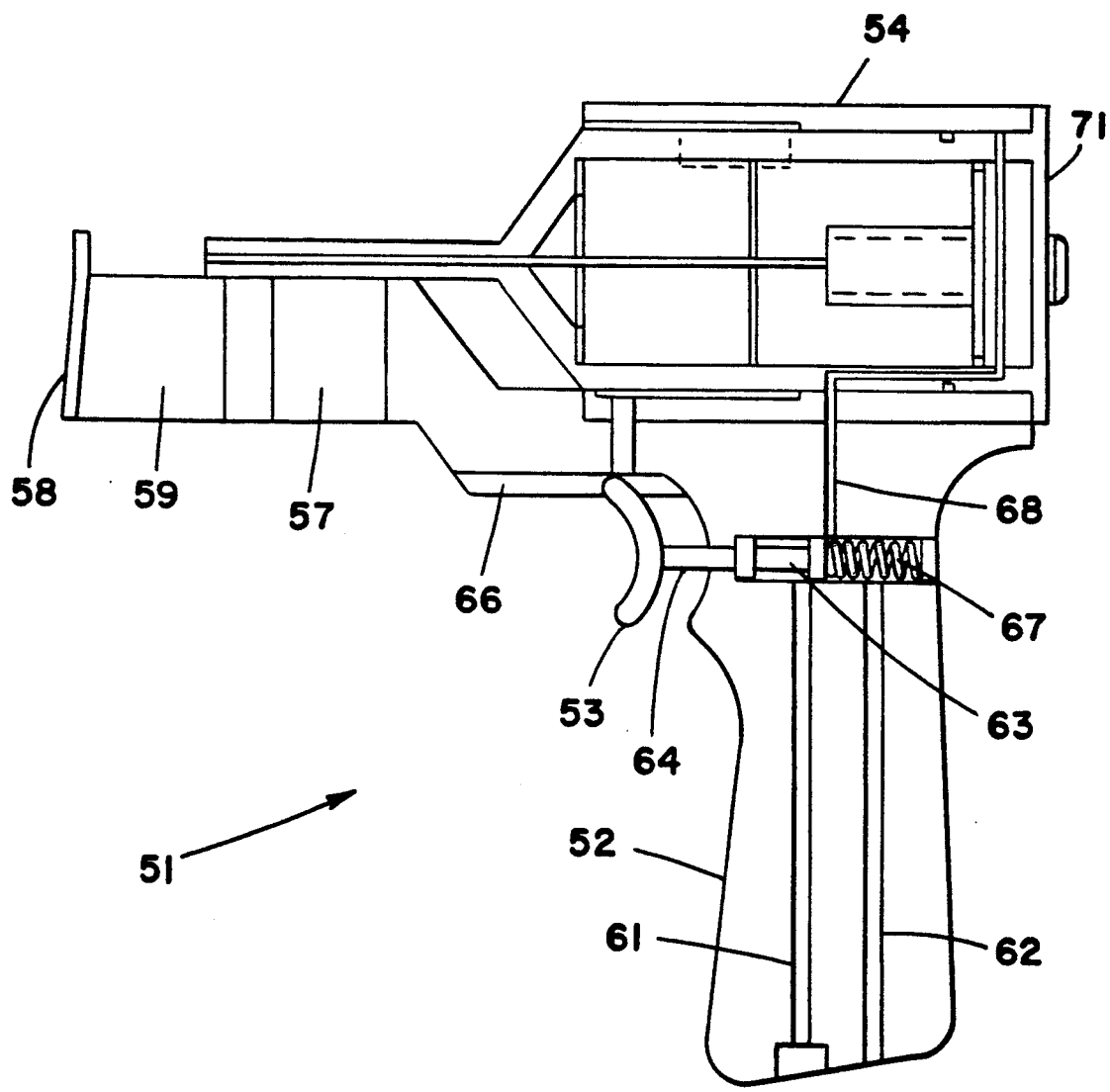
FIG_6

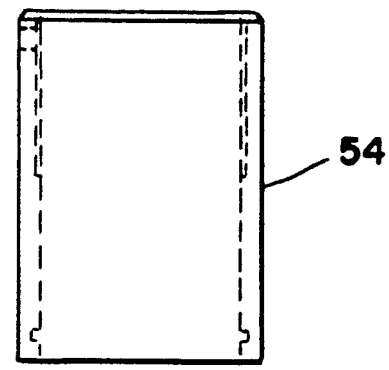
FIG_7
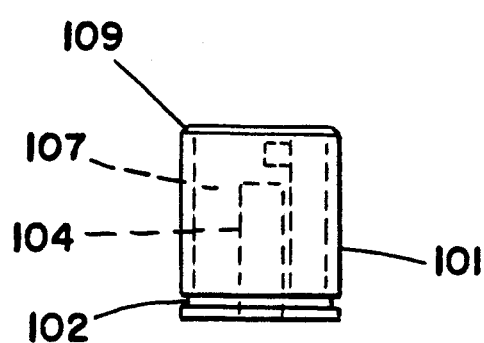
FIG_10
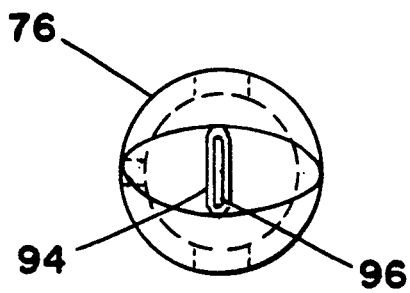
FIG_8
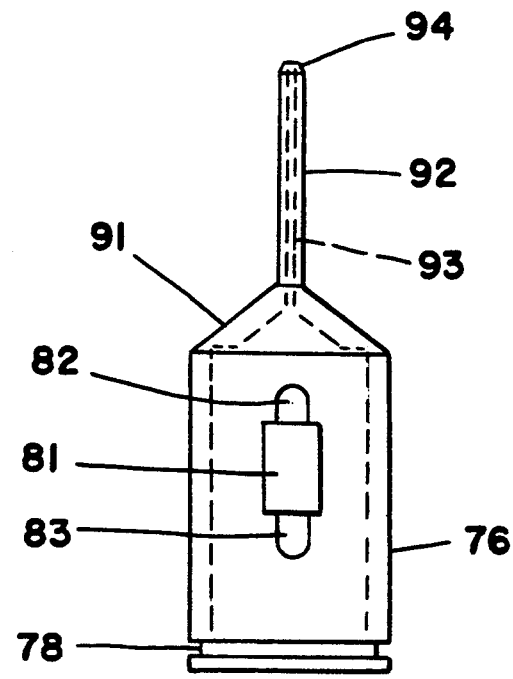
FIG_9

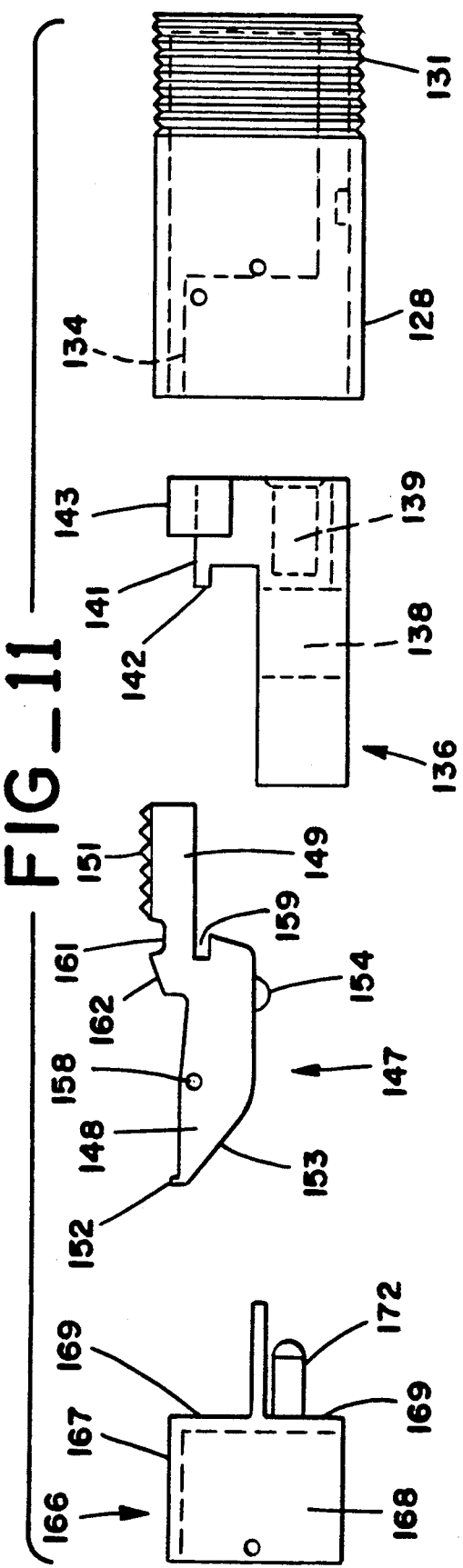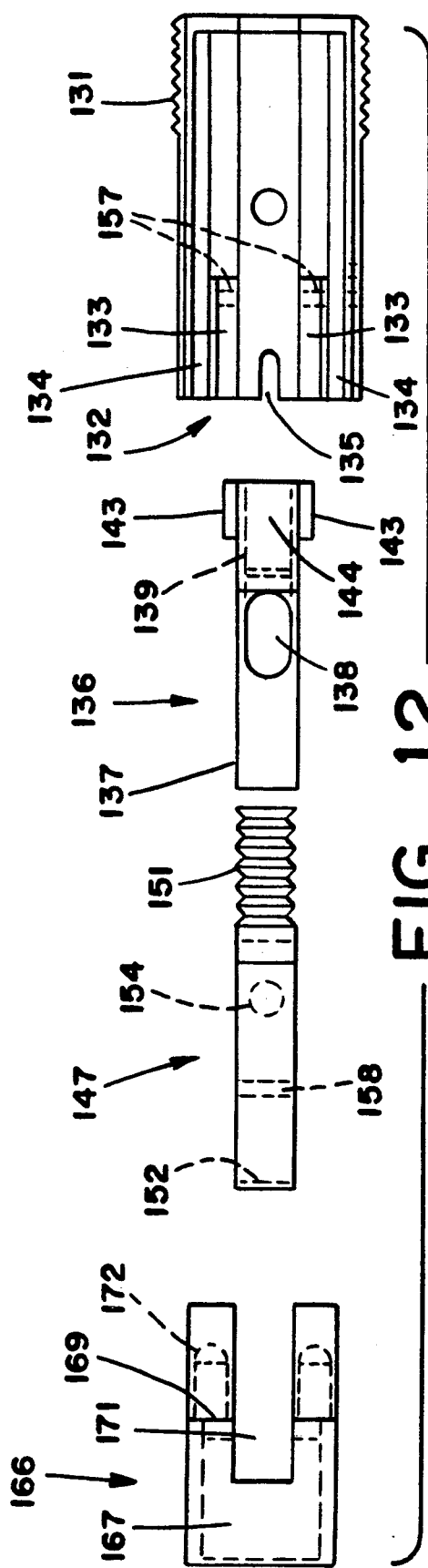

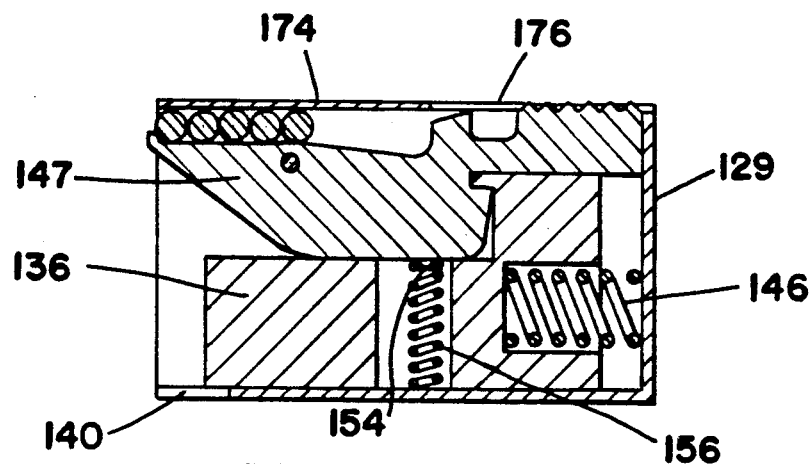
FIG_14
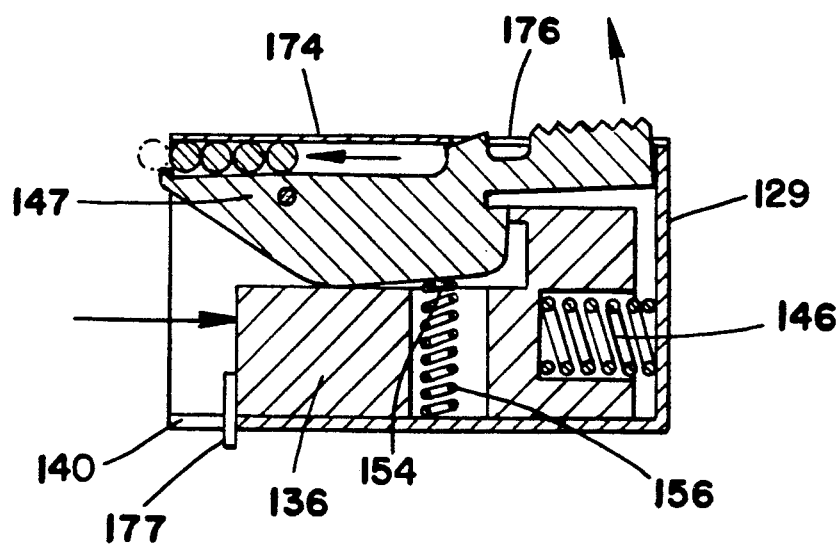
FIG_15
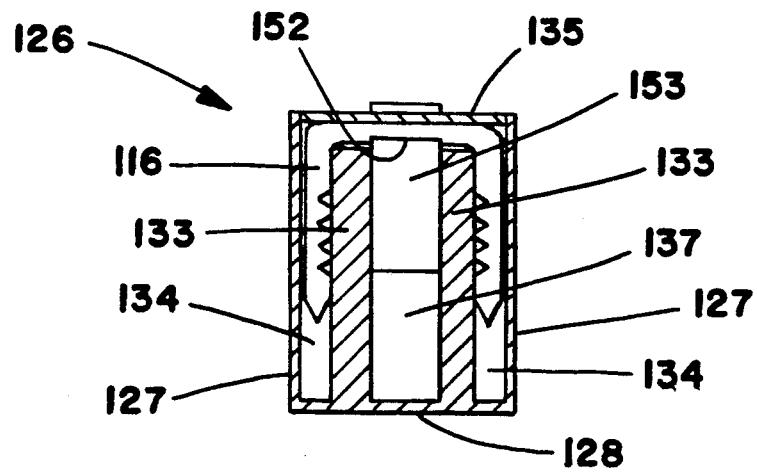
FIG_13

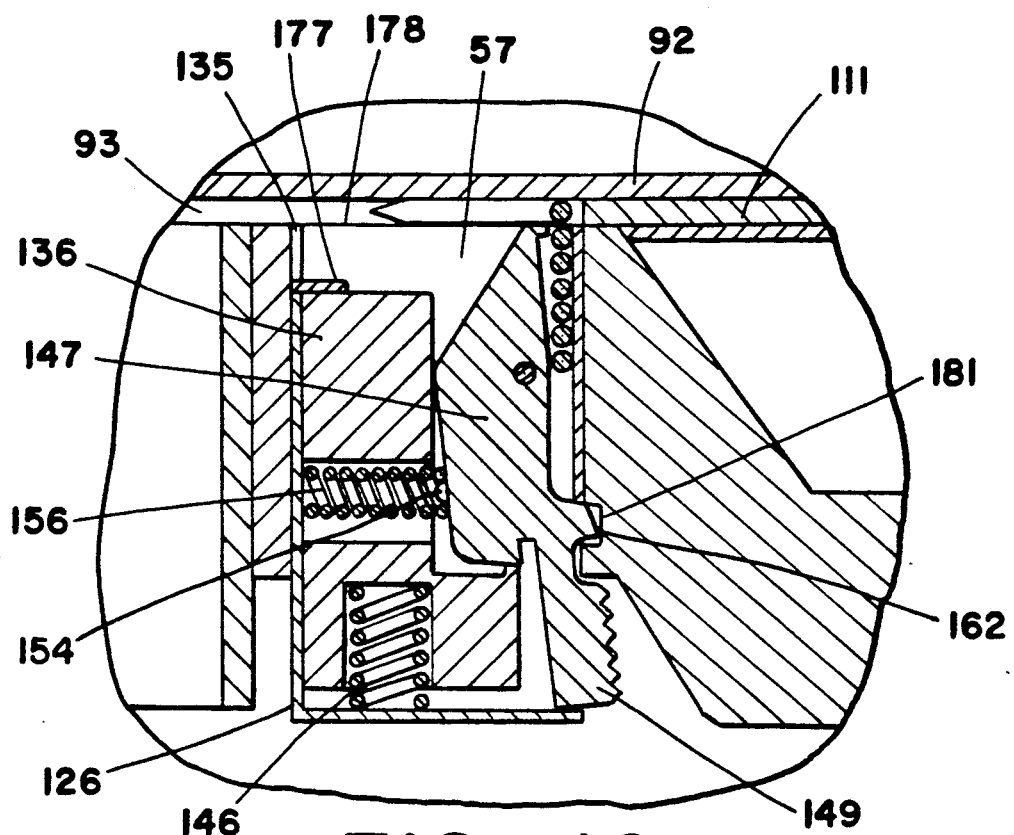
FIG_16
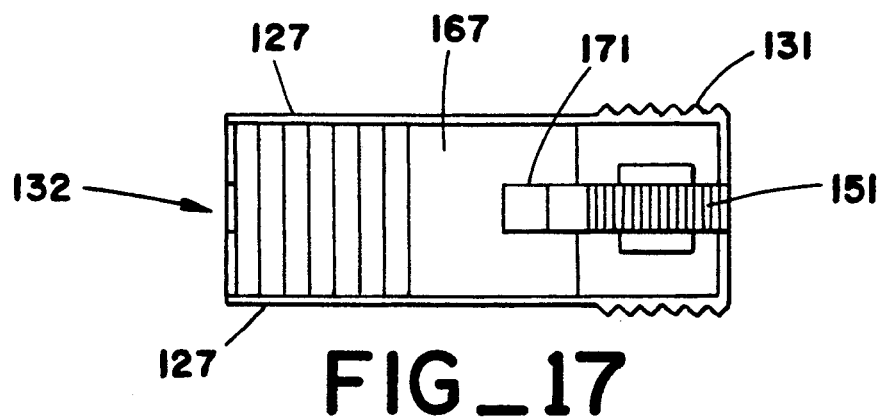
FIG_17
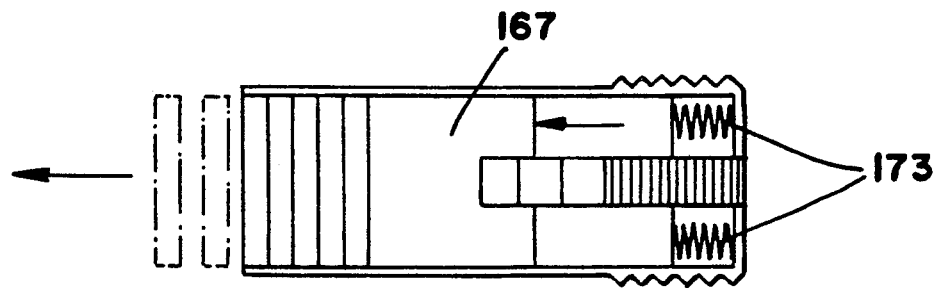
FIG_18

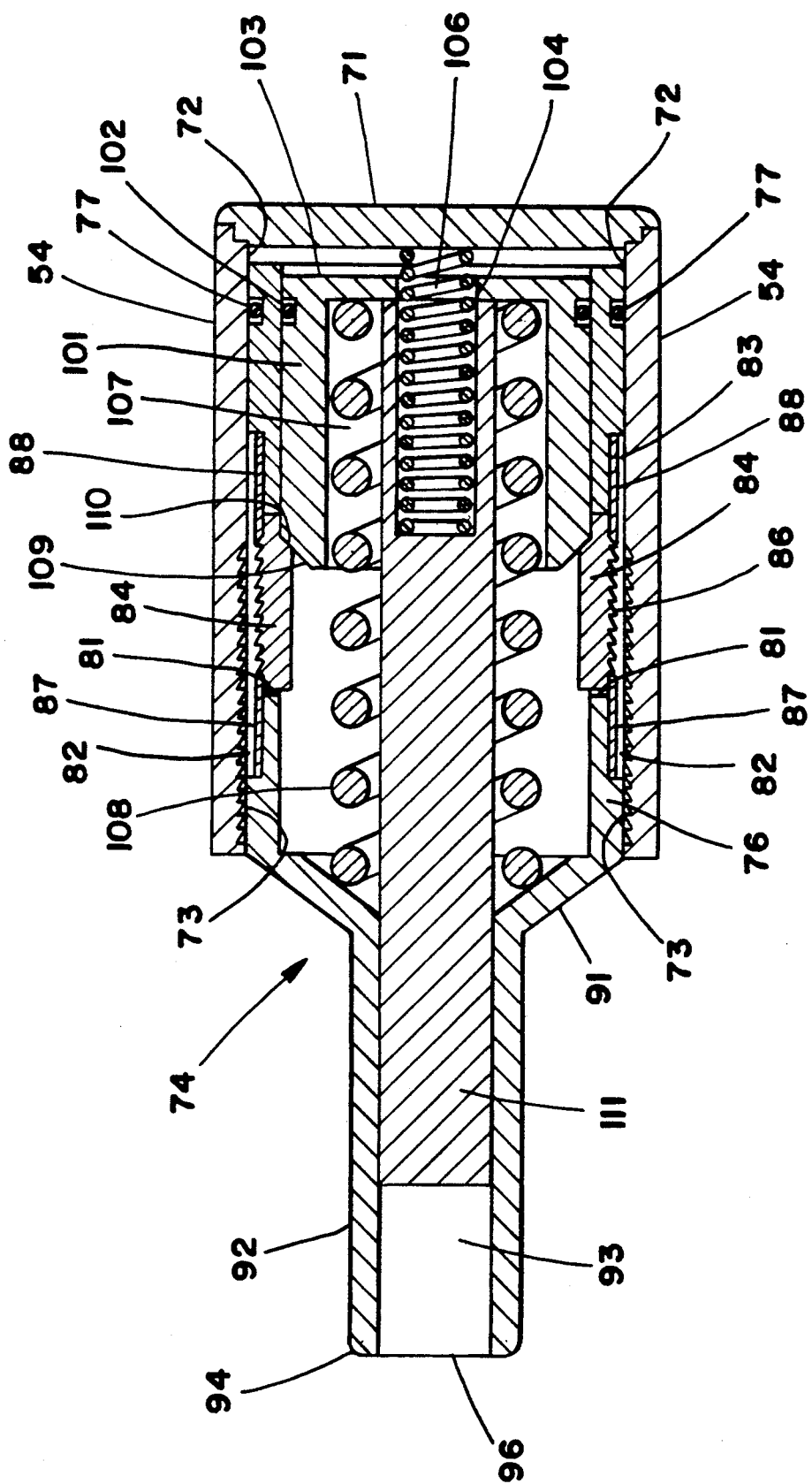
FIG_19

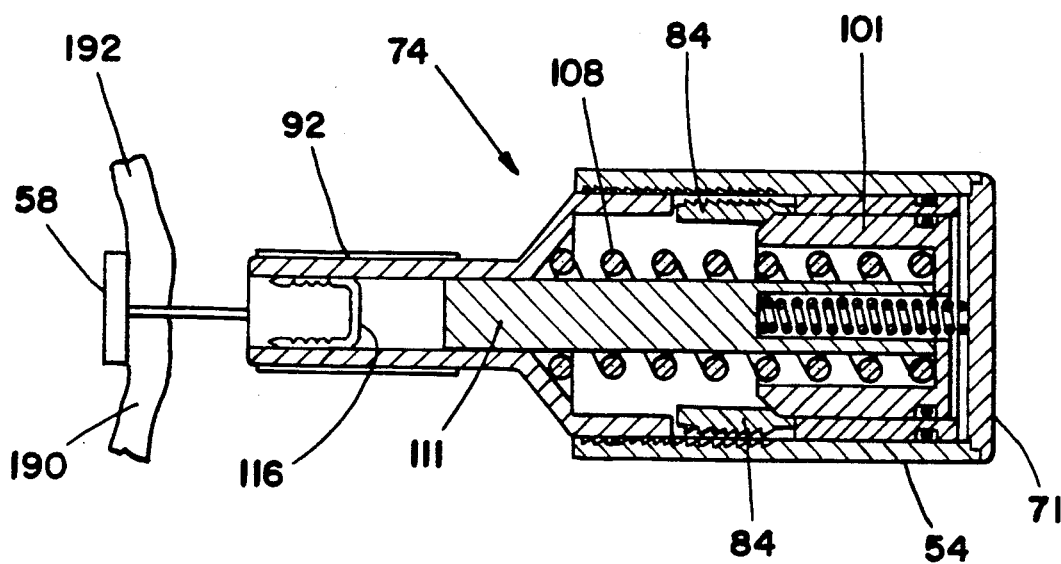
FIG_20
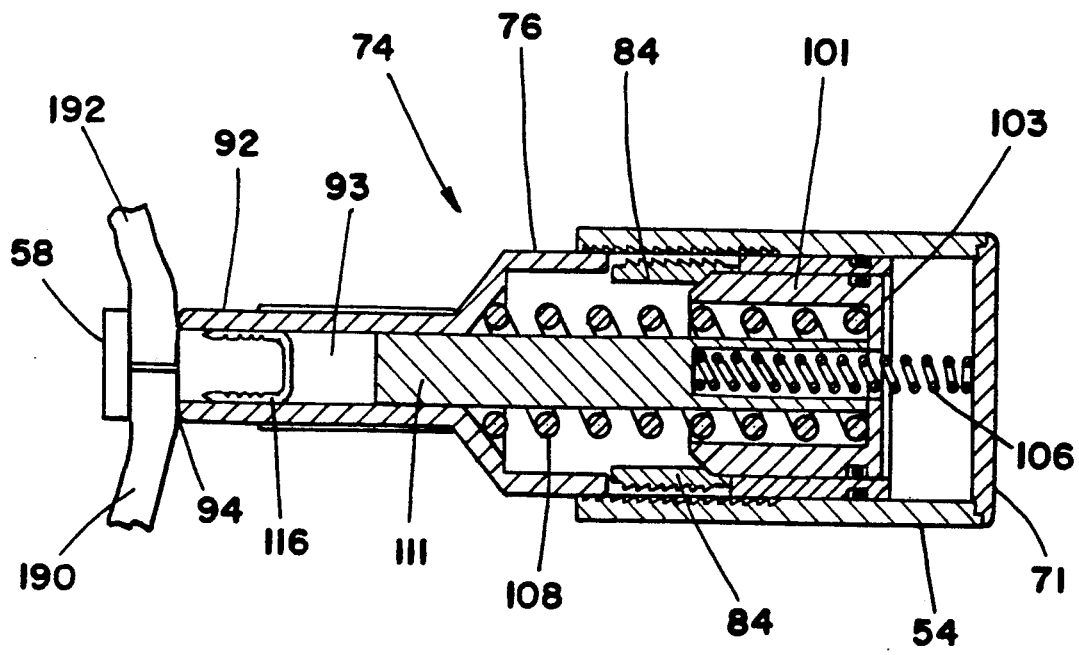
FIG_21

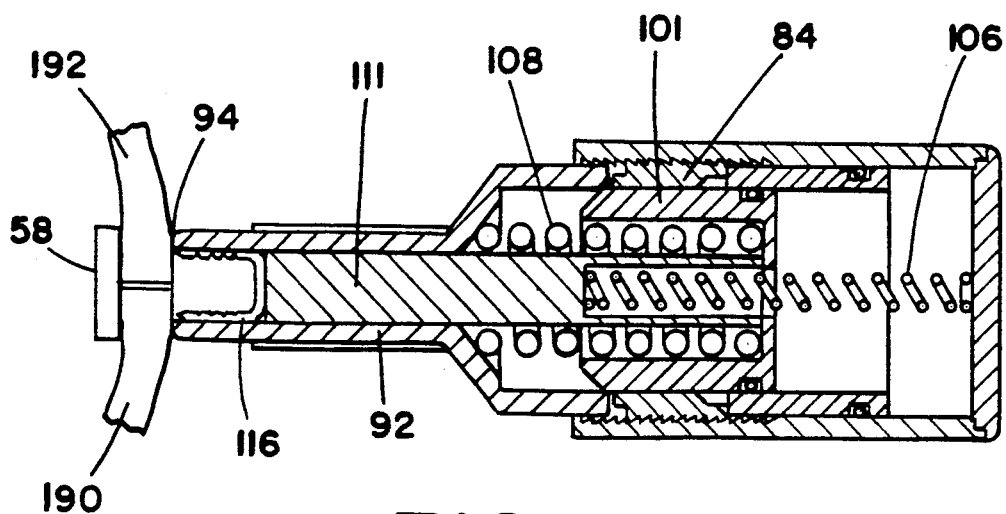
FIG_22
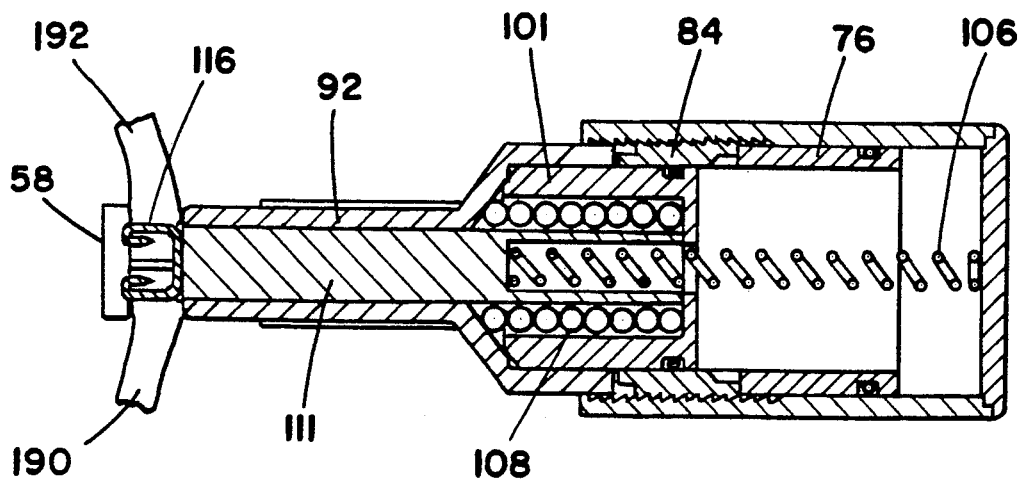
FIG_23
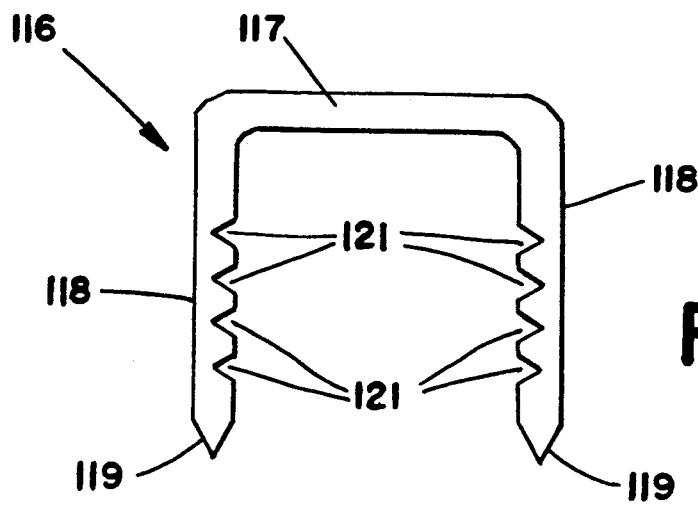
FIG_33

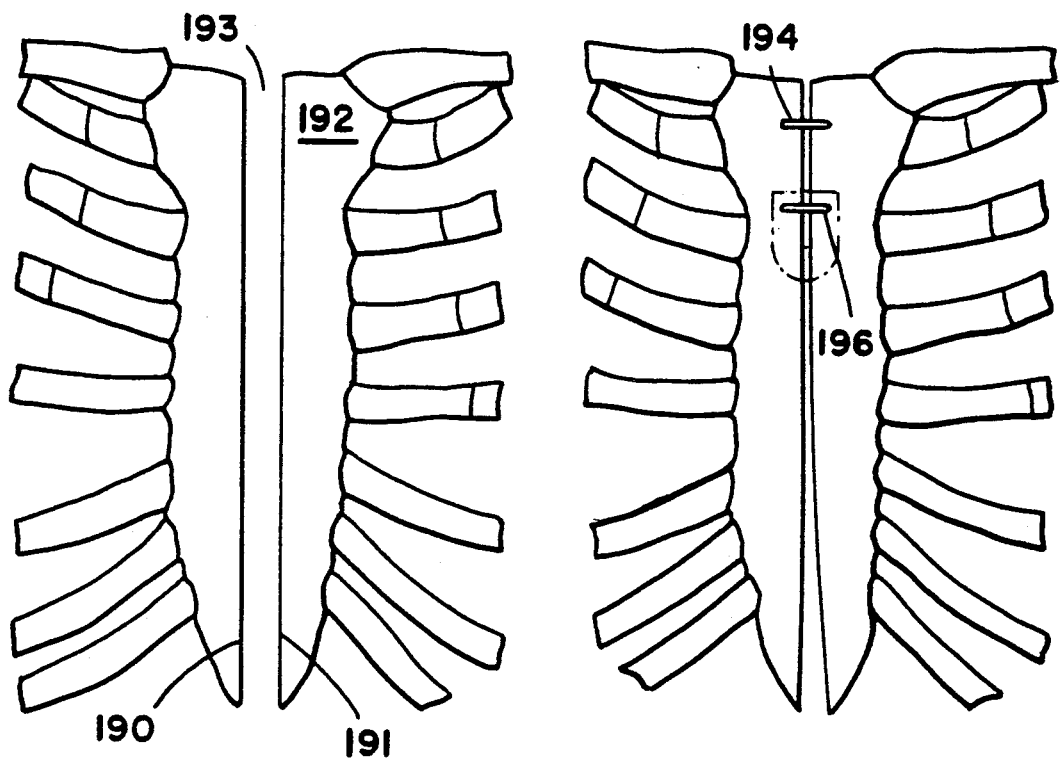
FIG_24  FIG_25
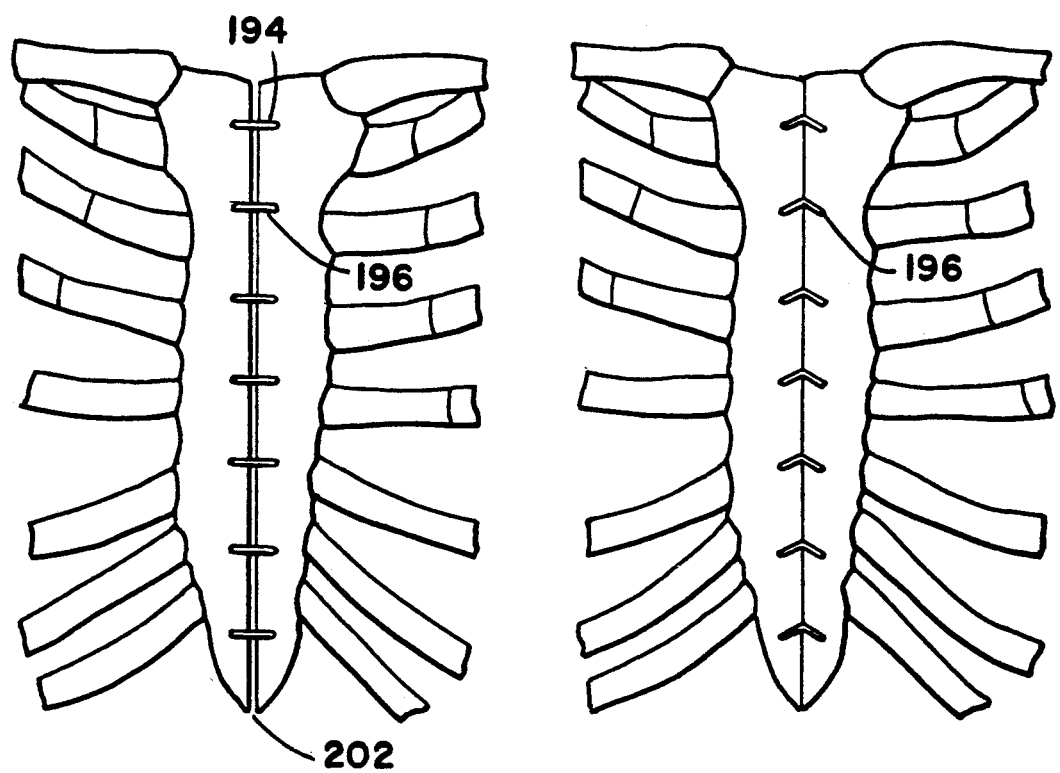
FIG_26  FIG_27

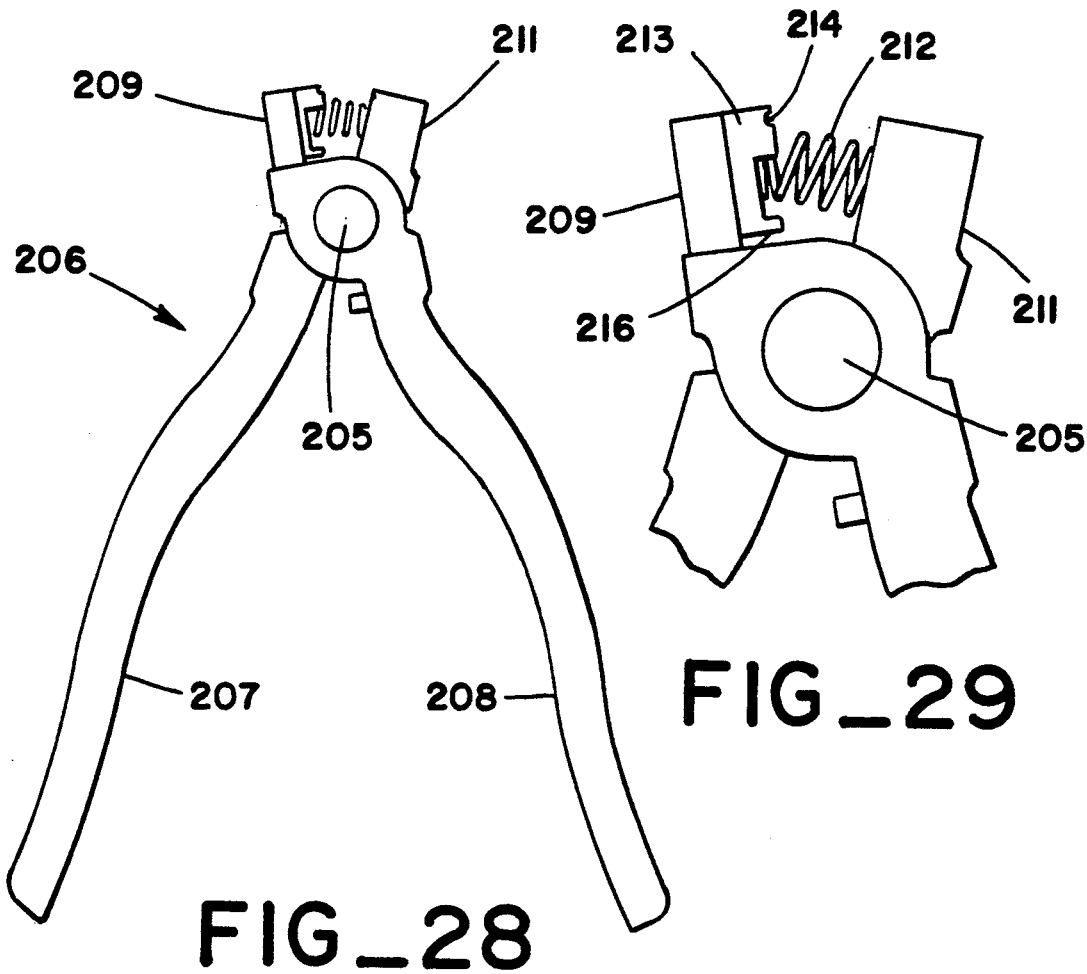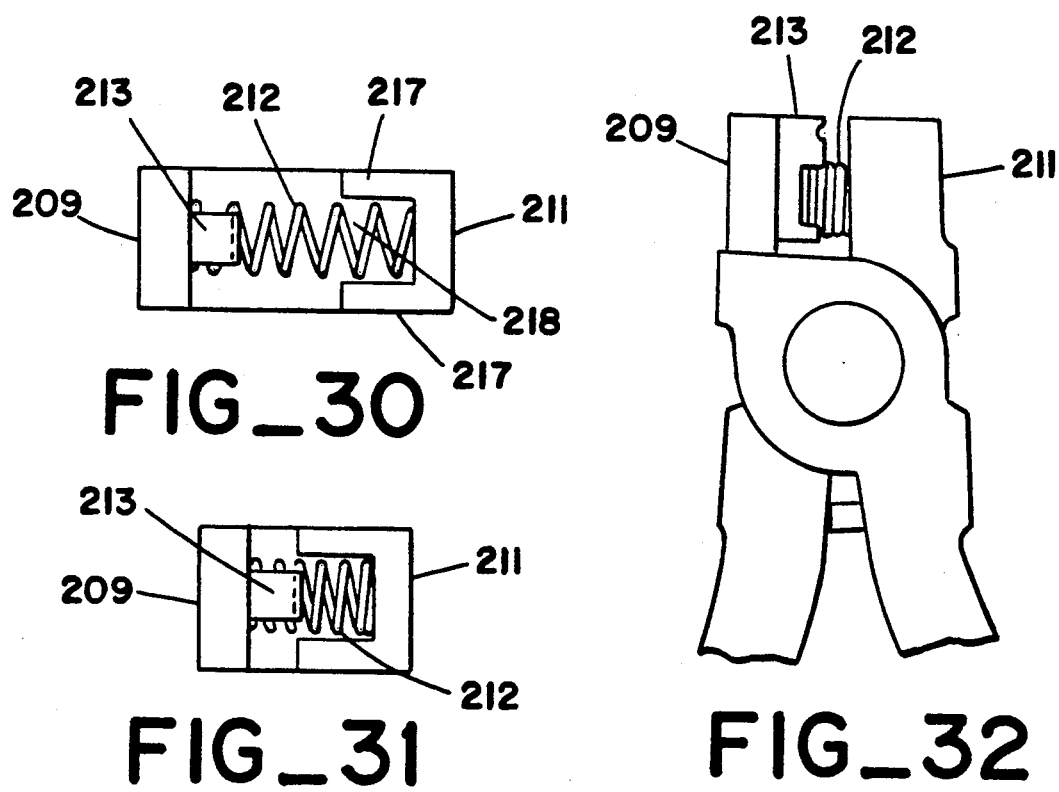

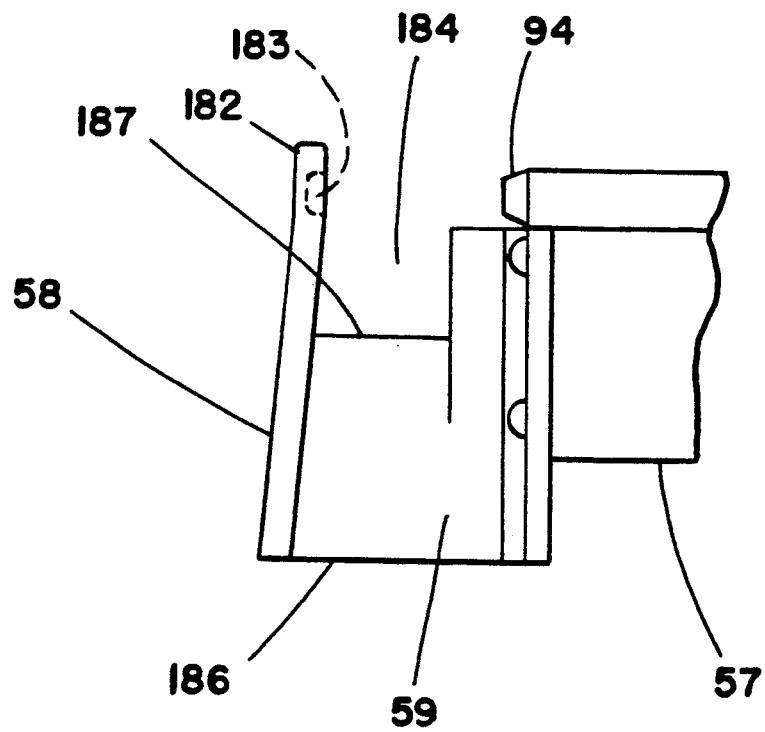
FIG_34
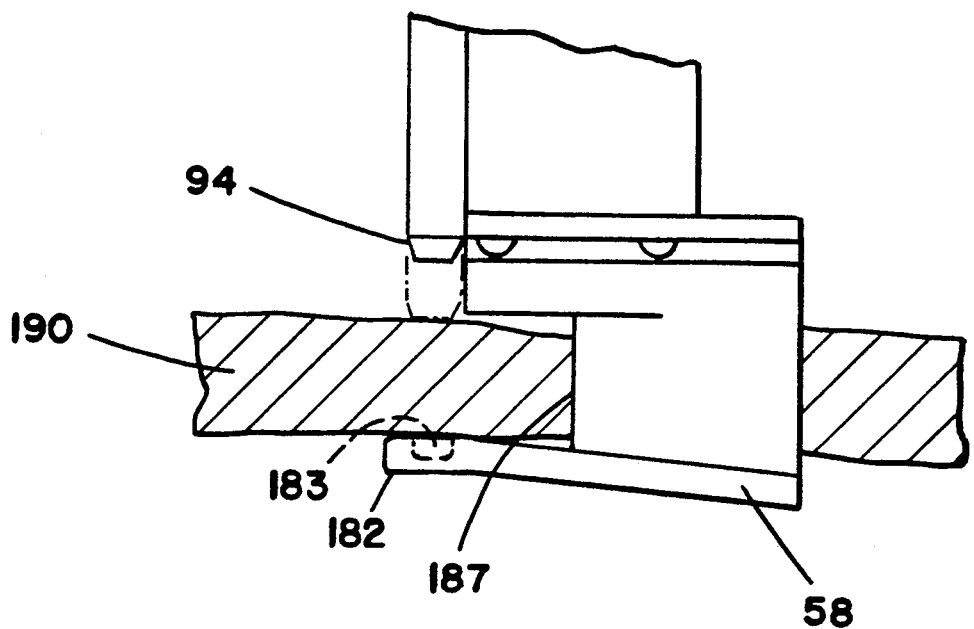
FIG_35

STERNUM STAPLING APPARATUS

BACKGROUND OF THE INVENTION

A large proportion of cardiac disease cases involve occlusions of the coronary arteries which become sufficiently servere to cause angina, infarction, and ultimately, death. One of the most effective therapies for occlusive coronary disease is the coronary bypass surgical procedure, in which a section of vascular tissue is harvested from the patient and grafted between the aorta and the coronary artery or arteries to bypass the occluded portion(s) of the artery. Attesting to the effectiveness of this procedure is the fact that more than 250,000 coronary bypass procedures are undertaken annually in the United States alone, and many more hundreds of thousands of procedures are conducted worldwide.

The technique routinely used to gain access to the heart to install the bypass grafts involves opening the chest, cutting the sternum longitudinally and spreading the sternum laterally to open a pathway to the pericardium. After the grafts are installed, the sternum is rejoined and the skin and fascia are sutured to close the surgical wound. Joining the severed halves of the sternum is a major task, and is usually accomplished using strong metal wire similar in strength and diameter to piano wire. A large curved needle is employed to drive the wire through one half of the sternum adjacent to the cut edge, across the gap and up through the other half of the sternum. Thereafter the two ends of the wire are pulled to urge the two halves together, the wires are twisted to maintain the closure, and the excess wire is cut and removed. Generally speaking, from five to seven wire sutures are required to close the sternum, and this portion of the procedure may take as long as one-half hour.

It is a basic tenet of surgical practice that the longer a patient remains on the operating table, there is a statistically greater chance of complications and death. Therefor, it would be extremely beneficial to shorten the time required to close the sternum. However, there is no better and faster technique known in the prior art for rejoining the sternum.

In addition to coronary bypass surgery, there are many other surgical procedures that require opening the chest and cutting and rejoining the sternum in the same manner as coronary bypass procedures. These procedures would also benefit from an improved technique to close the sternum.

SUMMARY OF THE PRESENT INVENTION

The present invention generally comprises a method and apparatus for stapling together adjacent bone tissue in surgical procedures. More specifically, the invention is designed to join the severed sternum portions of a typical open chest surgical procedure, and to do so quickly, permanently, and easily. The invention thus comprises an important advance over the prior art technique of using wire sutures to close the severed sternum.

One aspect of the apparatus of the invention includes a staple anvil formed on a shoe member which extends from the tool and is supported on a thin web member. The shoe is adapted to be disposed beneath the sternum with the web member extending between the severed sternum sections. The tool includes a staple driver which urges each pointed leg of staple through a respective portion of the sternum and into impingement with the anvil. The anvil inlcudes a shaped surface which causes the pointed ends to curve retrograde and crimp into the underside of the sternum, so that the staple legs are permanently installed in the sternum and the staple web extends between the sternum sections and join them together.

Another aspect of the invention includes a staple driver mechanism for driving the staple through the sternum and into impingement with the anvil. The staple driver mechanism includes a pneumatic cylinder having a caliper member therein and an independent piston disposed concentrically within the caliper member. The inner bore of the cylinder includes locking threads therein, and the caliper includes a pair of windows with lock nuts disposed in the windows and spring-biased inwardly to avoid engagement with the locking threads. The caliper includes a nose portion extending distally therefrom towards the anvil shoe, with a slot in the nose portion dimensioned to receive a staple driver which extends distally from the piston. When pneumatic pressure is applied to the proximal ends of the caliper and the piston, both members are driven distally in the cylinder. As the caliper is moved distally, the nose first impinges on the sternum, stopping the caliper while the piston continues to advance. The advancing piston drives the lock nuts outwardly to engage the locking threads, locking the caliper in place and protecting the sternum from further pneumatic force.

The piston continues to advance, translating the staple driver through the caliper nose slot to drive a staple into the sternum. When the piston has translated fully into the caliper, the staple driver has completed driving the staple into the anvil and crimping the staple legs. Thereafter, springs disposed within the caliper and cylinder urge the caliper and piston proximally to return to their quiescent positions. The caliper thus serves to locate the surface of the sternum with respect to the tool nose, and to initiate staple driving when the sternum surface is contacted by the caliper nose. Thereafter, all pneumatic force is applied only to the staple driver, so that all force is directed to the staple itself, and the sternum is not subjected to any further squeezing force. Furthermore, full translation of the staple driver is limited by the piston bottoming out in the caliper assembly, and at that point the distal end of the staple driver is disposed at the nose opening of the caliper assembly. Thus the staple driver cannot impinge on the sternum itself, and the sternum is protected by the locking nut mechanism from bruising or damage from contact by the caliper assembly or the staple driver assembly.

In a further aspect of the invention, there is provided a staple cartridge for storing sternum staples and dispensing the staples singularly and serially into the path of the staple driver. The staple cartridge includes a housing dimensioned to store the requisite number of staples for one procedure (e.g., 5–7 staples) in a stacked column, and a staple pusher to urge the staple column toward a dispensing end of the cartridge. The tool is provided with a housing adjacent to the caliper nose, the housing including a chamber shaped to receive the dispensing end of the staple cartridge. Within the staple cartridge there is provided a latch member which serves both to secure the cartridge within the chamber, and also to prevent discharge of the staples from the cartridge when the cartridge is not within the chamber.

The chamber is provided with a pin extending therein and disposed to be engaged in a slot in the cartridge as the cartridge is inserted, the pin causing the latch to be released to retain the cartridge in the chamber and at the same time release the staple column so that the staple pusher urges the endmost staple of the column into the path of the staple driver.

Another aspect of the invention comprises a tool for adjusting the proximation of the sternum portions joined by the staples. The adjusting tool is a pliers-like tool having a pair of handle member joined at a pivot, and a pair of jaws extending from the handle members. The jaws are brought together as the handles are squeezed together. One jaw includes a pair of lugs which are spaced to impinge on the web of a sternum staple at locations adjacent to the legs of the staple, and the other jaw is provided with a single lug to impinge on the medial portion of the same staple web. After the staple is installed in the sternum, the adjusting tool jaws may be engaged with the staple web, and the handles squeezed to impinge the lugs in confronting relationship. The pair lugs bend the web about the single lug, the bend effectively decreasing the linear distance between the staple legs and urging the sternum portions into closer impingement.

The apparatus of the invention also includes the sternum staples which are designed to be formed and crimped into the sternum. Each staple includes a wire web and a pair of legs extending integrally from the opposed ends of the web. Each leg is provided with a plurality of notches disposed in confronting relationship to the opposite leg, the notches being positioned to determine the locations at which the leg bends and crimps when the leg tip strikes the anvil of the stapler tool. The notches assure that the leg tip bends retrograde and is driven into the underside of the sternum, so that there is no risk of exposing the tissue beneath the sternum to the staple points.

The method of the present invention includes the installation of staples into a previously severed sternum, each leg of the staple engaging a respective half of the sternum adjacent to the severing line, and the staple web linking the severed halves in impinging opposition. The method also includes the step of bending the webs of the staples after they are installed in the sternum portions, whereby the sternum portions may be urged together in abutting relationship. The method of the invention further includes the provision of the stapler tool and cartridge and the operation of these components to effect installation of the staples in the severed sternum portions.

BRIEF DESCRIPTION OF THE DRAWING

FIG. 1 is a side elevation of the sternum stapling tool of the present invention.

FIG. 2 is a top view of the sternum stapling tool shown in FIG. 1.

FIG. 3 is a front end elevation of the sternum stapling tool depicted in FIGS. 1 and 2.

FIG. 4 is a back end elevation of the sternum stapling tool shown in FIGS. 1-3.

FIG. 5 is a bottom view of the sternum stapling tool of FIG. 1-4.

FIG. 6 is a cutaway side elevation of the sternum stapling tool of the present invention.

FIG. 7 is a plan view of the caliper cylinder of the sternum stapling tool.

FIG. 8 is a front end view of the caliper of the sternum stapling tool.

FIG. 9 is a plan view of the caliper of the sternum stapling tool.

FIG. 10 is a plan view of the piston of the sternum stapling tool.

FIG. 11 is an exploded side view of the staple cartridge assembly of the present invention.

FIG. 12 is an exploded end view of the staple cartridge assembly of the present invention.

FIG. 13 is a top view fo the staple cartridge shown in FIGS. 11 and 12.

FIGS. 14 and 15 are schematic, sequential view showing the operation of the latch mechanism in the staple cartridge.

FIG. 16 is an enlarged, cross-sectional elevation showing the staple cartridge engaged in the cartridge chamber of the sternum stapling tool.

FIGS. 17 and 18 are sequential end views showing staples being dispensed from the staple cartridge.

FIG. 19 is a cross-sectional top view of the stapler driving mechanism of the sternum stapling tool, shown in the quiescent position.

FIGS. 20-23 are a sequence of cross-sectional top views of the stapler driver mechanism, showing the action of the component parts in installing a staple in a sternum.

FIGS. 24-27 are a sequence of plan views showing the joining of a severed sternum according to the method of the present invention.

FIG. 28 is a plan view of the staple adjusting tool of the present invention.

FIG. 29 is an enlarged fragmentary side view of the jaws of the staple adjusting tool of FIG. 28, shown in the open position.

FIG. 30 is a fragmentary top view of the jaws of the staple adjusting tool, shown in the open position.

FIG. 31 is a fragmentary top view of the jaws of the staple adjusting tool, shown in the closed position.

FIG. 32 is an enlarged fragmentary side view of the jaws of the staple adjusting tool of FIG. 28, shown in the closed position.

FIG. 33 is a plan view of the sternum staple construction of the present invention.

FIG. 34 is an enlarged side elevation of the shoe portion of the staple applying tool of the present invention.

FIG. 35 is an enlarged vertical elevation showing the show portion of the staple applying tool in operating position relative to the sternum.

DESCRIPTION OF THE PREFERRED EMBODIMENT

A major aspect of the apparatus of the present invention is a sternum stapling tool 51 shown in FIGS. 1-6. In the preferred embodiment the tool 51 is provided with a pistol-like configuration, although the active components of the tool may be joined in other functional formats. The major components of the tool 51 includes a pistol handle 52 and an actuating trigger 53, and a housing 54 secured to the upper end of the handle 52. A bracket 56 extends distally from the handle 52, and a staple cartridge chamber 57 is formed in the bracket. Extending distally from the chamber portion of the bracket is a staple-forming shoe 58. The shoe 58 is joined to the bracket by a thin web 59.

With reference to FIG. 6, the handle 52 includes a pair of pneumatic channels 61 and 62 longitudinally therein from the butt of the handle to a spool valve 63. The valve spool is joined to the trigger 53 by an actuating rod 64, and a portion of the trigger is disposed in a slot 66 extending parallel to the axis of the housing 54. The trigger is disposed to be squeezed manually and to translate along the slot 66, urging the valve spool to translate against a restoring spring 67. The valve 63 controls the flow of pneumatic pressure from the input channel 61 through a feed channel 68 to the proximal interior of housing 54, the channel 62 comprising a vent channel that is normally open when the valve 63 is in the unactuated position.

With reference to FIGS. 6-10 and 19, the housing 54 generally comprises a tubular member having an end cap 71 secured to the proximal end in a sealing engagement. The interior of the housing 54 includes a cylinder 72 having a generally smooth bore. However, the medial-distal surface of the cylinder is provided with annular threads 73, the threads being configured as fine pitch buttress threads which taper proximally. The invention also includes a caliper assembly 74 assembled to the housing 54. The caliper assembly 74 includes a cylindrical portion 76 dimensioned to be received in the bore 72 in close-fit tolerance, with an O-ring 77 secured in a groove 78 about the proximal end of the cylindrical portion 76 to form a sliding seal engagement with the bore.

A significant feature of the caliper assembly is a pair of windows 81 (FIGS. 9 and 19) extending through the sidewall of the cylindrical portion 76 and disposed in diametrical opposition. Each window 81 is provided with a rectangular plan configuration, with a pair of blade spring pockets 82 and 83 formed in the outer surface of the cylindrical portion 76 and disposed at longitudinally opposed ends of each window 81. A pair of lock nuts 84 are also provided, each lock nut having a rectangular plan configuration dimensioned to fit in one of the windows 81 with free clearance, and having a curvature substantially the same as the portion of the cylinder sidewall represented by the window 81. The outer surface of each lock nut is provided with fine pitch buttress threads 86 oriented to engage and mate with the threads 73 of the bore 72. Disposed in each of the spring pockets 82 and 83 are a pair of blade springs 87 and 88, each disposed to engage a respective end of a respective lock nut 84 and urge the lock nut resiliently inwardly, so that the threads 86 thereof do not engage the threads 73 of the bore 72.

The caliper assembly 74 also includes a conical end wall 91 joined to the distal end of the cylindrical portion 76 and tapering distally. A nose portion 92 extends distally from the tapered end of the wall 91 and is oriented generally coaxially with the bore 71 and the cylindrical portion 76 of the caliper assembly. The nose portion 92 is provided with the geometric configuration of a rectangular prism, and includes a rectangular slot 93 extending coaxially and longitudinally therein. The distal end 94 of the nose portion 92 is beveled, and the slot 93 exits therefrom at an outlet window 96.

Disposed concentrially within the caliper assembly 74 is a piston assembly 101. The piston assembly is dimensioned for close tolerance, sliding fit within the cylindrical portion 76 of the caliper assembly, and is provided with an O-ring 102 adjacent to the proximal end to form a sliding seal with the interior surface of the portion 76. The piston assembly 101 includes a proximal end face 103 having a bore 104 extending axially therein. A helical extending spring 106 is disposed in the bore 104 and secured at opposed ends to the piston assembly and the end cap 71.

The distal end of the piston assembly 101 includes an annular chamber 107 formed concentrically therein. A helical compression spring 108 extends within the caliper assembly, the proximal end of the spring 108 being disposed in the chamber 107 and the distasl end impinging on the interior of the end wall 91 of the caliper assembly. The distal end of the piston also includes a beveled edge 109. The axial length of the piston assembly is dimensioned so that in the unactuated position the proximal end thereof is generally flush with the proximal end of the caliper assembly, and the beveled edge 109 is impinging on complementary oblique surface 110 of the lock nuts 86.

The piston assembly further includes a staple pusher 111 extending distally from the distal end of the piston. The staple pusher comprises a rectangular bar having a width dimensioned to be received within the slot 93 in freely sliding relationship, and a length dimensioned so that the distal end is disposed in a medical portion of the slot 93 in the unactuated position of the piston assembly.

With regard to FIG. 33, the invention also includes a unique staple adapted to be used in conjuction with the tool of the invention to rejoin the servered portions of a sternum, or the like. The staple 116 comprises a wire member including a transverse web 117 and a pair of staple legs 118 extending integrally from opposed ends of the web. The legs 118 are generally parallel and orthogonal to the web, and the distal ends of the legs are provided with sharp points 119. A significant feature of the staple 116 is the provision of a pluality of notches 121 formed in mutually confronting surfaces of the legs 118. The notches are spaced along the length of each leg at predetermined positions to define the zones at which each leg bends during the stapling process of the invention. The notches 121 also provide relief so that the wire may be bent back upon itself without causing fracture or spalling at the outside surface of each bend. The forming and bending of each staple is described in the following description.

With regard to FIGS. 13-18, the invention provides a staple cartridge 126 for supplying a plurality of staples 116 to the staple applying tool 51. It may be appreciated that a group of staples 116 are provided in each cartridge 126, and that the staples may be selectively varied in length to accommodate the variation in thickness of differing portions of the sternum. The cartridge 126 comprises a generally rectangular assembly having a opposed side walls 127 extending orthogonally from a bottom wall 128. An end wall 129 joins the edges of the side and bottom walls at one edge of the cartridge, and the side walls 127 are provided with a plurality of ridges 131 adjacent to the end wall 129 for handling purposes. The other end 132 of the cartridge comprises the staple dispensing end.

With regard to FIGS. 12 and 13, the cartridge includes a pair of interior walls 133 extending from the bottom wall 128, each spaced from the respective adjacent side wall 127 to define a track 134 dimensioned to accommodate the legs of a pluality of staples 116 disposed in a stacked column. The walls 133 extend parallel to the walls 127 from the dispensing end 132 a short distance toward the medial portion of the cartridge, forming tracks 134 sufficiently long to accommodate approximately five to seven staples 116, although the cartridge may be lenghtened to store as many staples as required. The two tacks 134 are joined by a track position 135 which accommodates the web portions of the staples 116. The bottom wall 128 is also provided with an actuating slot 140 extending into the distal end thereof, for purposes to be explained in the following description.

The cartridge assembly also includes a detent bracket 163, comprising a generally rectangular block 137 dimensioned to be slidablky received between the interior walls 133. The block 137 includes a passageway 138 extending through a medial portion thereof, and a spring hole 139 extending into the proximal end thereof. The proximal end of the bracket 136 also includes a portion 141 having an increased height, and a detent 142 extending distally therefrom. A pair of panels 143 extend upwardly from opposed sides of the portion 141 to define therebetween a recess 144. A compression spring 146 is disposed in the hole 139 to resiliently urge the bracket 136 toward the distal end of the cartridge.

The cartridge assembly further includes a latch member 147 having a length slightly greater than the bracket 136 and disposed directly adjacent thereto, and a similar width, as shown in FIGS. 14–18. The latch member is an irregularly shaped solid generally comprising a body portion 148 and a tab portion 149 extending proximally therefrom. The tab portion 149 is dimensioned to be received in the recess 144 between the panels 143 of the bracket 136. The tab portion includes ridges 151 on the upper exterior surface for handling purposes. The body portion 148 includes a generally smooth upper surface, with a lip 152 formed at the distal end thereof. The lower surface of the body portion is generally parallel to the upper surface, with the distal lower surface 153 tapering toward the distal lip 152. A spring keeper 154 it extends from the lower surface, and is positioned to retain the upper end of a helical compression spring 156 which is disposed within the hole 138 of the bracket 136. The latch member 147 is secured in rotating fashion between the interior walls 133 by a pivot pin extending through aligned holes 157 in the interior walls and through hole 158 in the latch member.

The latch member embodies two distinct latch functions. A latch recess 159 formed at the junction of the body and tab portions 148 and 149 is disposed to engage the detent 142 of the bracket assembly 136. Furthermore, the upper surface of the tab portion includes a latch 161 having a lip 162 extending obliquely therefrom. These latch functions are described in the following specification.

A further component of the staple cartridge is a staple pusher 166. The staple pusher includes side walls 168 extending from a top wall 167 in spaced apart, orthogonal relationship. The side walls spacing is dimensioned so that the side walls 168 are disposed in the staple tracks 134, and the top wall 167 is abutting the transverse web of the proximal endmost staple 116 in the cartridge. An end wall 169 extends between the side walls 168, and a medial slot 171 is formed in the top wall 167 and the end wall 169. The slot 171 provides clearance for the latch member and the bracket member, so that the spring pusher 166 translates longitudinally in the cartridge. A pair of spring keepers 172 extend proximally from the end wall 169 to retain like ends of a pair of compression springs 173 which impinge the proximal end of the cartridge. The springs 173 urge the staple pusher 166 and the column of staples toward the distal dispensing end of the cartridge.

Secured to the top of the staple cartridge is a top panel 174 which encloses the top of the cartridge and retains the staples 116 therein. A slot 176 extends medially in the top at the proximal end thereof to permit the tab portion 149 and the latch 161–162 to extend from the cartridge. When the tab portion is in its quiescent, retracted disposition, as shown in FIG. 14, the lip 152 at the distal end of the latch member is rotated into the track portion 135, blocking the track 135 and preventing discharge of any staples 116 from the cartridge.

With regard to FIG. 16, the chamber 57 of the staple applying tool 51 is a rectangular opening dimensioned to receive the cartridge 126 in close fit, with the dispensing end 132 disposed innermost in the chamber 57. An actuating pin 177 extends into the chamber 57 at the inner end thereof, and is positioned to be received in the actuating slot 140 of the cartridge 126 as the cartridge is fully inserted in the chamber. The pin 177 impinges on the distal end of the bracket 136, urging the bracket 136 to translate against the force of spring 146. The movement of the bracket 136 causes the detent 142 to release from the latch recess 159, permitting the latch member 147 to be urged by the spring 156 to pivot about hole 158 (FIG. 15). The rotation is an excursion of only a few degrees, and it is sufficient to move the lip 152 out of blocking position in the track 135 so that end distal-most staple 116 in the track may be discharged from the cartridge. It should be noted that the inner end of the chamber 57 is open, and the nose portion 92 is provided with an opening 178 extending into the slot 93, so that the endmost staple dispensed from the cartridge is pushed into the slot 93, and into the feed path of the staple driver 111.

The chamber 57 is further provided with a detent recess 181 formed in an outer portion of the proximal wall thereof. The recess is disposed so that full insertion of the cartridge 126 in the chamber 57 brings the latch 161 into registration with the detent recess 181. When the actuating pin 177 causes the detent 142 to release the latch member 146, rotation of the latch member 146 urges the latch 161 into the recess 181, retaining the cartridge in the chamber 57. To remove the cartridge, the tab portion 149 is manually urged to rotate into the cartridge until the latch 161 is released from the recess 181. At the same time, the spring 146 urges the bracket assembly toward the dispensing end of the cartridge, and the detent 142 engages the recess 159 of the latch member to secure the latch member in the quiescent position of FIG. 14. The distal translation of the bracket assembly against the actuating pin 177 also acts to urge the cartridge out of the chamber, so that removal of the cartridge is initially aided by the force of spring 146. Furthermore, rotation of the latch member 147 into the quiescent position brings the lip 152 into blocking position in the staple track 135, retaining any staples 116 remaining in the cartridge.

With reference to FIGS. 1–6 and 34, the shoe 58 of the present invention is supported by a web 59 extending distally from the tool. The web includes a cutout portion 184 between the anvil and the caliper nose, and the remainder of the web 59 tapers from the lower edge 186 to a knife edge 187. The web is thus configured to be inserted between confronting edges of adjacent portions of sternum, and to permit abutment of the confronting edges in the area into which a staple is installed.

The shoe includes an anvil portion 182 disposed in confronting, spaced relationship to the end 94 of the nose portion 92 of the caliper assembly 74. The anvil portion 182 is provided with a staple forming groove 183 extending parallel to the slot opening 96 and disposed to receive the pointed ends of each staple delivered by the staple driver 111. The groove 183 is provided with a rounded inner surface fashioned to form the staple legs by turning the pointed ends inwardly each toward the other. The grooves 123 in the staple legs act cooperatively with the forming groove 183 to direct the pointed ends of the staple legs into a retrograde bend, extending proximally toward the caliper assembly 74.

Operation of the Staple Applying Tool

To employ the staple applying tool 51, the tool input line 61 is first connected to a source of pneumatic pressure, preferably a regulated gas supply in the range of 50-100 psi. A staple cartridge 126 is then placed in the chamber 57 (FIGS. 1 and 16), and fully inserted so that the latch member 147 is actuated to retain the cartridge in the chamber and to dispense the endmost staple into the feed path of the staple driver 111, as described previously. With regard to FIGS. 24 and 35, the web 59 of the tool is then inserted between the confronting edges 190 and 191 of the severed sternum 192, with the shoe 58 disposed beneath the sternum and interposed between the sternum and the organs of the thoracic cavity. The tool is placed at the ends 193 of the severed sternum edges, and the edges are brought into abutment using standard surgical techniques and tools. It should be noted that the cutout 184 of the web 59 permits abutment of the confronting edges of the sternum in the area between the nose end 94 and the forming groove 183. Thereafter, the trigger 53 is actuated to drive the first staple 194 into the sternum, each leg of the staple penetrating a respective confronting edge portion of the sternum and joining them together.

The operation of the staple installing mechanism is shown sequentially in FIGS. 20-23. The components are initially in the unactuated positions shown in FIGS. 19 and 20, with the endmost staple disposed in the feed path of the slot 93. When the trigger is actuated, pneumatic pressure introduced through passage 68 urges both the caliper assembly 74 and the piston assembly 101 to translate distally in the cylinder bore 72. Spring 108 is compressed, and spring 106 is extended by the translations of the caliper and piston assemblies. The staple 116 is carried distally by the caliper assembly, and the distal end of the staple driver 111 is spaced slightly proximally from the staple.

When the distal end 94 of the caliper assembly impinges on the sternum 192 (FIG. 21), the caliper assembly is blocked from further translation, while the piston assembly is free to continue translation under pneumatic force. The piston assembly 101 begins to move distally relative to the caliper assembly, the beveled edge 109 of the piston driving the lock nuts radially outwardly (FIG. 22) to engage the lock threads 73 of the cylinder. This action prevents further distal translation of the caliper assembly, and limits the force applied by the caliper assembly to the sternum to a few pounds of pressure. However, the pneumatic pressure continues to drive the piston distally, urging the staple driver 111 to impinge on the web of staple 116 and drive the sharp pointed legs of the staple through the sternum and into forming groove 183 of the anvil. Due to the placement of the grooves 123 in the staple legs and to the inclined surfaces of the forming groove, the staple legs are directed to bend inwardly toward each other, and to bend into a retrograde direction, as shown in FIG. 23, as the staple driver completes its advancement. The piston 101 reaches its limit of travel, and the trigger is released. Spring 106 pulls the piston proximally toward the unactuated position, and spring 108 restores the initial spacing between the caliper and piston assemblies. As the piston 101 approaches its proximal quiescent position, the lock nuts 84 are freed from engagement, and the leaf springs 87 and 88 urge the lock nuts radially inwardly in preparation for the next dispensing cycle.

It should be noted that the caliper assembly will stop its distal translation upon contact with the sternum, regardless of the thickness of the sternum of the patient or variations in thickness in an individual patient, without injuring the sternum. Furthermore, as soon as the caliper assembly is halted, the staple driver begins to advance relative to the caliper assembly and drive the staple through the sternum. The caliper thus serves to locate the surface of the sternum with respect to the tool nose, and to initiate staple driving when the sternum surface is contacted by the caliper nose. Thereafter, all pneumatic force is applied only to the staple driver, while the caliper remains locked, so that all force is directed to the web of the staple itself, and the sternum is not subjected to any further squeezing force. Furthermore, full translation of the staple driver is limited by the piston bottoming out in the caliper assembly, and at full translation the distal end of the staple driver is disposed at the nose opening of the caliper assembly. Thus the staple driver cannot impinge on the sternum itself, and the sternum is protected by the locking nut mechanism from bruising or damage from both contact by the caliper assembly or penetration by the staple driver assembly.

The tool 51 is then translated incrementally along the severance line of the sternum, the edges 190 and 191 adjacent to the tool are urged into abutment, and another staple 196 is installed through the sternum portions as described above. This process is repeated until 5-7 staples are installed (FIG. 26), or as many as are required to rejoin the sternum completely and effectively. The tool is then withdrawn from the end 202 of the severance, leaving the sternum rejoined along the entire length of the severance. The staples are formed of a biologically compatible material such as stainless steel or the like, and are intended to remain permanently installed. It should be noted that the points of the staples are all bent into a retrograde configuration, so that there are no abrasive or irritating metal projections to inflame tissue beneath the sternum. The entire staple installing process requires only a few minutes to complete, and saves at least 15 minutes of time compared to prior art sternum wire suturing manual techniques.

Although the installed staples should secure the confronting sternum portions together with sufficient pressure to insure prompt healing, it may become necessary to increasing the abutting force of the confronting edges. With regard to FIGS. 28-32, the invention provides a pliers-like tool 206 including handles 207 and 208 joined at a pivot 205. Opposed jaws 209 and 211 are secured to handles 208 and 207, respectively, so that squeezing the handles together brings the jaws together with a mechanical advantage. A spring 212 is disposed between the jaws (or may be disposed between the handles) to bias the jaws and handles toward the open disposition.

The jaw 209 is provided with a narrow lug 213 extending toward the jaw 211, the lug 213 including a flat end face having a groove 214 extending laterally across the face. The groove 214 has a sufficient diameter to receive the web portion 117 of a staple 116. The jaw 209 also includes a stop 216 extending toward the opposing jaw. The jaw 211 is provided with a C-shaped anvil 217 having a cavity 218 opening toward the jaw 209. The cavity 218 is sufficiently wide to receive the lug 213 therein when the handles are squeezed together and the jaws are engaged (FIG. 32).

To use the tool 206, the web 117 of a staple 194, 196, etc that has been installed in the sternum is placed between the confronting lug 213 and anvil 217 of the tool jaws, with the web 117 disposed in the groove 214. The handles are then squeezed together, urging the lug 213 toward the anvil 217. The staple web is caught between the anvil pressing on opposed ends of the web and the lug pressing on the medial portion thereof, and the staple web 117 is deformed from its normally linear configuration to a slightly bent configuration. This action causes the staple legs 118 to be moved closer together in terms of linear distance therebetween, urging the sternum sections closer together (FIG. 27). This effect may be controlled by gauging the manual pressure applied to the handles. The stop 216 of jaw 209 prevent excessive bending of the staple web. The staple web is sufficiently stiff and strong to retain the configuration imparted by the tool 206. The tool 206 may be applied selectively to any of all of the staples installed in the sternum, as deemed necessary by the surgeon.

We claim:

1. A stapling tool assembly for joining two members having confronting adjacent edges and like first sides and opposed second sides, comprising an anvil portion disposed at said like first sides of the two members and which has a central region that spans said confronting edges of the two members, said anvil portion having opposite end regions each of which is situated behind a separate one of said two members, at least one substantially U-shaped staple having a pair of leg regions joined at one end by a bridging region of the staple, staple applying means disposed at said opposed second sides of the two members for establishing a path of travel for said staple and for driving each of said leg regions of said staple through a separate one of said two members to impinge each of said leg regions of said staple on a separate one of said end regions of said anvil portion, and a web extending between the confronting edges of the two members, said web joining said central region of said anvil portion and said staple applying means, wherein said web is a thin flat element having a knife edge facing said path of travel of said staple to permit abutment of said confronting edges of said two members prior to driving of said staple through said two members.

2. A stapling tool assembly for joining two members having confronting adjacent edges and like first sides and opposed second sides, comprising an anvil portion disposed at said like first sides of the two members and which has a central region that spans said confronting edges of the two members, said anvil portion having opposite end regions each of which is situated behind a separate one of said two members, at least one substantially U-shaped staple having a pair of leg regions joined at one end by a bridging region of the staple, staple applying means disposed at said opposed second sides of the two members for driving each of said leg regions of said staple through a separate one of said two members to impinge each of said leg regions of said staple on a separate one of said end regions of said anvil portion, and a web extending between the confronting edges of the two members, said web joining said central region of said anvil portion and said staple applying means, wherein said staple applying means includes a housing having a chamber therein, a caliper having a cylindrical portion which extends into said chamber and a nose portion which extends out of said housing and towards said anvil portion and which forms a track for said staple, said caliper being translatable relative to said housing to travel said nose portion towards said anvil portion, a staple driving member extending within said caliper and being movable relative thereto to travel said staple along said track, drive means for selectively translating said caliper and staple driving member towards said two members, and means for stopping travel of said caliper when said nose portion contacts at least one of said two members while enabling continued travel of said staple driving member.

3. The staple applying tool assembly of claim 2, wherein said reciprocal drive means includes a fluid-driven piston.

4. The staple applying tool assembly of claim 3, further including caliper means for housing said staple driving member.

5. The staple applying tool assembly of claim 2, further including a plurality of staples and further including a staple magazine for storing said plurality of staples and dispensing said staples singly and serially into a feed path of said staple driving member.

6. The staple applying tool assembly of claim 5, wherein said staple magazine comprises a staple cartridge, and means for removably securing said staple cartridge to said staple applying means.

7. A stapling tool assembly for joining two members having confronting, adjacent edges and like first sides and opposed second sides, comprising an anvil portion disposed at said like first sides of the two members, staple applying means disposed at said opposed second sides of the two members for driving at least one staple through both said members to impinge on said anvil portion, and web means extending between the confronting edges of the two members, said web means joining said anvil portion and said staple applying means, wherein said staple applying means includes a staple driving member, and reciprocal drive means for translating said staple driving member toward said two members wherein said reciprocal drive means includes a fluid-driven piston, further including caliper means for housing said staple driving member and wherein said caliper means includes a cylinder portion disposed coaxially with said piston and in which said piston is slidable, wherein said caliper means further includes a nose portion extending from said cylinder portion, said nose portion having a slot extending therealong and dimensioned to receive said staple driving member therein in freely translating fashion, wherein said cylinder portion of said caliper means includes an end surface that is fluid driven in concert with said piston.

8. A stapling tool assembly for joining two members having confronting, adjacent edges and like first sides and opposed second sides, comprising an anvil portion disposed at said like first sides of the two members, staple applying means disposed at said opposed second sides of the two members for driving at least one staple through both said members to impinge on said anvil portion, and web means extending between the confronting edges of the two members, said web means joining said anvil portion and said staple applying means, wherein said staple applying means includes a staple driving member, and reciprocal drive means for translating said staple driving member toward said two members wherein said reciprocal drive means includes a fluid-driven piston, further including caliper means for housing said staple driving member and wherein said caliper means includes a cylinder portion disposed coaxially with said piston and in which said piston is slidable, wherein said caliper means further includes a nose portion extending from said cylinder portion, said nose portion having a slot extending therealong which slot is dimensioned to receive said staple driving member therein in freely translating fashion, wherein said cylinder portion of said caliper means is slidably disposed in a bore of said staple applying tool, said cylinder portion having a curved sidewall and further including at least one window opening extending through said curved sidewall.

9. The staple applying tool assembly of claim 8, further including at least one lock nut disposed in said at least one window opening, and resilient means for biasing said lock nut radially inwardly to avoid impingement on said bore.

10. The staple applying tool assembly of claim 13, wherein said lock nut has an outer surface that faces outwardly at said window opening and wherein said lock nut includes locking threads disposed on the outer surface thereof in confronting relationship to said bore, and said bore includes complementary locking threads in confronting relationship to said window opening.

11. The staple applying tool assembly of claim 10, wherein said piston includes beveled surface means for translating relative to said caliper means and engaging said at least one lock nut and driving said at least one lock nut radially outwardly to engage said complementary locking threads and immobilize said caliper means.

12. A stapling tool assembly for joining two members having confronting, adjacent edges and like first sides and opposed second sides, comprising an anvil portion disposed at said like first sides of the two members, staple applying means disposed at said opposed second sides of the two members for driving at least one staple through both said members to impinge on said anvil portion, and web means extending between the confronting edges of the two members, said web means joining said anvil portion and said staple applying means, wherein said reciprocal drive means includes a staple driving member, and reciprocal drive means for translating said staple driving member towards said two members, further including a plurality of said staples and a staple magazine for storing said plurality of staples and dispensing said staples singly and serially into a feed path of said staple driving member, said staple magazine having a staple cartridge and means for removably securing said staple cartridge to said staple applying means, wherein said means for removably securing said cartridge includes a latch member extendable from said cartridge and disposed to engage a detent recess in said staple applying means.

13. The staple applying tool assembly of claim 12, wherein said latch member is movable from a retracted disposition to an extended disposition to engage said detent recess of said staple applying means, said latch member including a latch lip means for preventing discharge of said staples from said cartridge when said latch member is in said retracted disposition.

14. A staple applying tool for joining confronting edges of a severed sternum which sternum has inner and outer surfaces, including a tool housing having a bore therein, means for driving a staple which staple driving means is secured in said bore in reciprocal fashion, a staple driving member extending from said staple driving means and translatable in reciprocal fashion from a proximal position through a feed path to a distal, staple applying position, staple magazine means having at least one staple therein and disposed to place said at least one staple into said feed path of said staple driving member, anvil means disposed to receive and form said at least one staple, means extending between said tool housing and said anvil means for supporting said anvil means spaced apart from said tool housing, whereby said tool housing and said staple driving member may be positioned adjacent to said outer surface of said sternum while said anvil means is supported adjacent to said inner surface of said sternum, wherein said staple driving means includes a piston disposed within said bore and fluid pressure means for urging said piston distally, and wherein said staple driving member is coupled to said piston, further including a caliper assembly, said caliper assembly including a cylindrical portion disposed concentrically within said bore and about said piston.

15. The staple applying tool of claim 14, wherein said caliper assembly includes a nose portion extending distally from said cylindrical portion, said nose portion including a slot extending therein through which said staple driving member extends in freely translating fashion.

16. The staple applying tool of claim 15, wherein said fluid pressure means also urges said caliper assembly distally.

17. The staple applying tool of claim 16, further including resilient means for opposing the distal translation of said caliper assembly and said piston and to restore said caliper assembly and said piston to proximal, unactuated positions.

18. The staple applying tool of claim 16, wherein said cylindrical portion of said caliper assembly includes at least one window opening in the curved sidewall thereof, and further including a lock nut disposed in said window opening.

19. The staple applying tool of claim 18, wherein said lock nut includes first locking threads disposed on the outer surface thereof in confronting relationship to said bore.

20. The staple applying tool of claim 19, wherein said bore is provided with second locking threads complementary to said first locking threads and engageable therewith.

21. The staple applying tool of claim 20, further including spring means for biasing said lock nut radially inwardly out of engagement with said second locking threads of said bore.

22. The staple applying tool of claim 21, wherein said piston includes means for impinging on said lock nut during distal motion relative to said caliper assembly, and for driving said lock nut radially outwardly through said window opening, whereby said first and second threads are engaged and said caliper assembly is immobilized in said bore.

23. The staple applying tool of claim 15, wherein said nose portion includes an opening into said slot for introducing a staple into said feed path of said staple driving member.

24. The staple applying tool of claim 23, wherein said tool housing includes a means for supporting said staple magazine means adjacent to said opening into said slot.

25. The staple applying tool of claim 24, wherein said staple magazine means includes a staple cartridge, and a plurality of staples stored within said cartridge.

26. The staple applying tool of claim 25, wherein said staple cartridge includes a cartridge housing having a staple discharge end, said staple discharge end disposed adjacent to said opening to said slot in said nose portion of said caliper member.

27. The staple applying tool of claim 26, further including a staple track disposed within said cartridge housing adjacent to said discharge end, said plurality of staples disposed in stacked, column fashion in said staple track, and staple pusher means for urging said plurality of staples toward said discharge end.

28. The staple applying tool of claim 27, further including a latch member secured in said cartridge housing, said latch member including a detent lip disposed to block said staple track at said discharge end to prevent discharge of said staples from said staple track.

29. The staple applying tool of claim 28, wherein said means for supporting said staple magazine means includes a chamber disposed adjacent to said nose portion of said caliper assembly and dimensioned to receive said cartridge housing.

30. The staple applying tool of claim 29, wherein said chamber includes a detent strike disposed therein.

31. The staple applying tool of claim 30, wherein said staple cartridge includes actuating means for operating said latch member to extend from said staple cartridge and engage said detent strike of said chamber, whereby said cartridge is retained in said chamber.

32. The staple applying tool of claim 31, wherein said extension of said latch member from said cartridge also causes said detent lip to move out of blocking position in said staple track, whereby said plurality of staples are dispensable from said discharge end of said staple track.

33. The staple applying tool of claim 32, wherein said actuating means includes an actuating pin extending from said tool housing into said chamber, said actuating pin disposed to impinge on a latch releasing member of said cartridge as said cartridge is inserted in said chamber.

* * * * *